(12) United States Patent
Tsujii et al.

(10) Patent No.: US 10,383,587 B2
(45) Date of Patent: Aug. 20, 2019

(54) RADIATION CT APPARATUS AND METHOD OF CONTROLLING THE SAME

(71) Applicant: CANON KABUSHIKI KAISHA, Tokyo (JP)

(72) Inventors: Osamu Tsujii, Kawasaki (JP); Tetsuo Shimada, Hachioji (JP); Sakiko Yamaguchi, Tokyo (JP); Takahiro Noguchi, Tokyo (JP); Hitomi Ogasawara, Kawasaki (JP); Chifuyu Inagaki, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 270 days.

(21) Appl. No.: 15/184,346

(22) Filed: Jun. 16, 2016

(65) Prior Publication Data

US 2017/0000434 A1 Jan. 5, 2017

(30) Foreign Application Priority Data

Jun. 30, 2015 (JP) ................................ 2015-131837

(51) Int. Cl.
*A61B 6/00* (2006.01)
*A61B 6/03* (2006.01)
*A61B 6/10* (2006.01)

(52) U.S. Cl.
CPC ............ *A61B 6/4435* (2013.01); *A61B 6/035* (2013.01); *A61B 6/105* (2013.01); *A61B 6/502* (2013.01); *A61B 6/032* (2013.01); *A61B 6/4085* (2013.01); *A61B 6/447* (2013.01); *A61B 6/547* (2013.01)

(58) Field of Classification Search
None
See application file for complete search history.

(56) References Cited

U.S. PATENT DOCUMENTS

| 4,969,167 A * | 11/1990 | Zupancic | A61B 6/035 378/10 |
| 7,315,606 B2 | 1/2008 | Tsujii | 378/20 |
| 7,945,015 B2 | 5/2011 | Tsujii et al. | 378/26 |
| 8,509,387 B2 | 8/2013 | Tsujii et al. | 378/146 |
| 9,295,438 B2 | 3/2016 | Omura et al. | A61B 6/4405 |
| 2005/0013403 A1 * | 1/2005 | Reznicek | A61B 6/035 378/15 |
| 2013/0163719 A1 | 6/2013 | Tsujii | 378/41 |

(Continued)

FOREIGN PATENT DOCUMENTS

| JP | H03-073111 U | 7/1991 |
| JP | 2000-083936 A | 3/2000 |

(Continued)

*Primary Examiner* — Hoon K Song
(74) *Attorney, Agent, or Firm* — Venable LLP

(57) ABSTRACT

A radiation CT apparatus includes a rotation unit configured to rotate about a rotation axis, a radiation generation unit and a radiation detector which are fixed on either side of the rotation axis in the rotation unit, and a gantry cover containing the radiation generation unit and the radiation detector and including a breast insert portion configured to insert a breast of an object. An opening portion that can be opened and closed is placed on the gantry cover of the radiation CT apparatus. The radiation generation unit and the radiation detector are stopped to form a space that allows a user to access the breast insert portion from the opening portion.

29 Claims, 10 Drawing Sheets

(56) References Cited

U.S. PATENT DOCUMENTS

| | | | | |
|---|---|---|---|---|
| 2014/0126689 A1* | 5/2014 | Hara | ............... | A61B 6/0407 |
| | | | | 378/19 |
| 2015/0216492 A1* | 8/2015 | Smith | ............... | A61B 6/10 |
| | | | | 378/209 |
| 2015/0272502 A1 | 10/2015 | Kaku et al. | ............... | A61B 5/6835 |
| 2016/0015344 A1* | 1/2016 | Fortuna | ............... | A61B 6/4435 |
| | | | | 378/51 |

FOREIGN PATENT DOCUMENTS

| | | | |
|---|---|---|---|
| JP | 2001-520434 A | 10/2001 | |
| JP | 2005-517486 A | 6/2005 | |
| JP | 2013-538668 T | 10/2013 | |
| WO | 2003/070101 A | 8/2003 | |
| WO | WO 2012/048000 A | 4/2012 | |

* cited by examiner

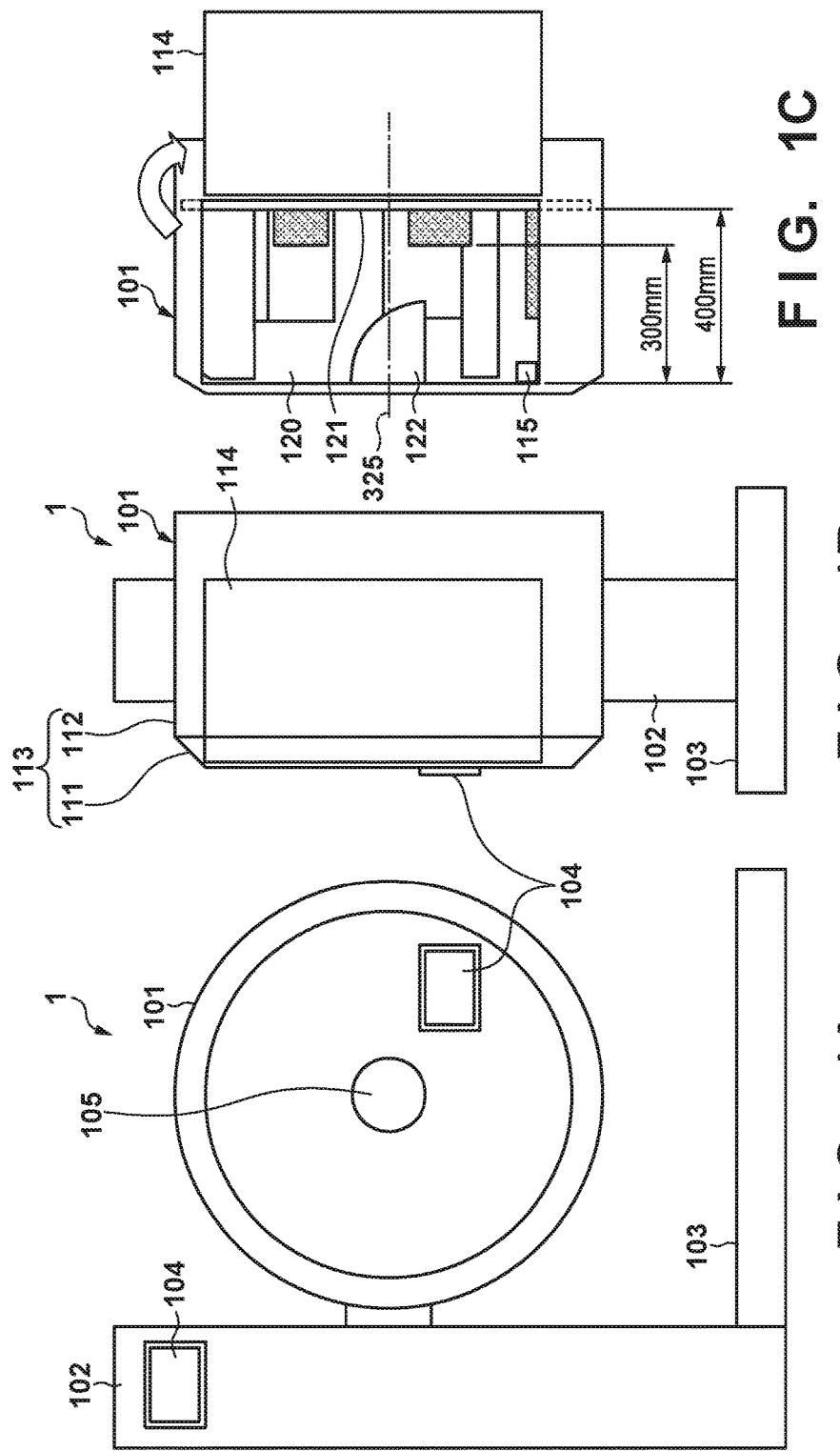

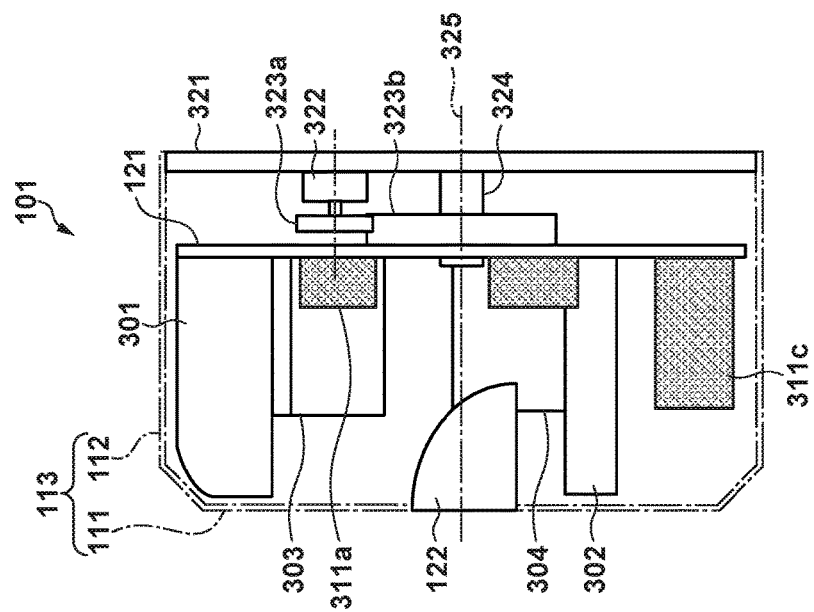
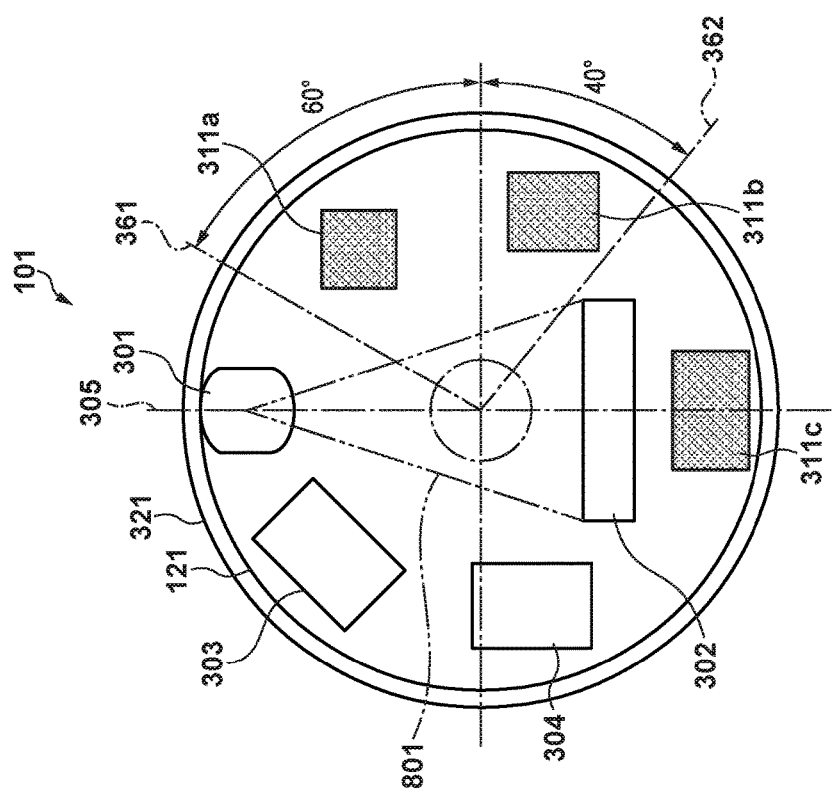
FIG. 3A
FIG. 3B

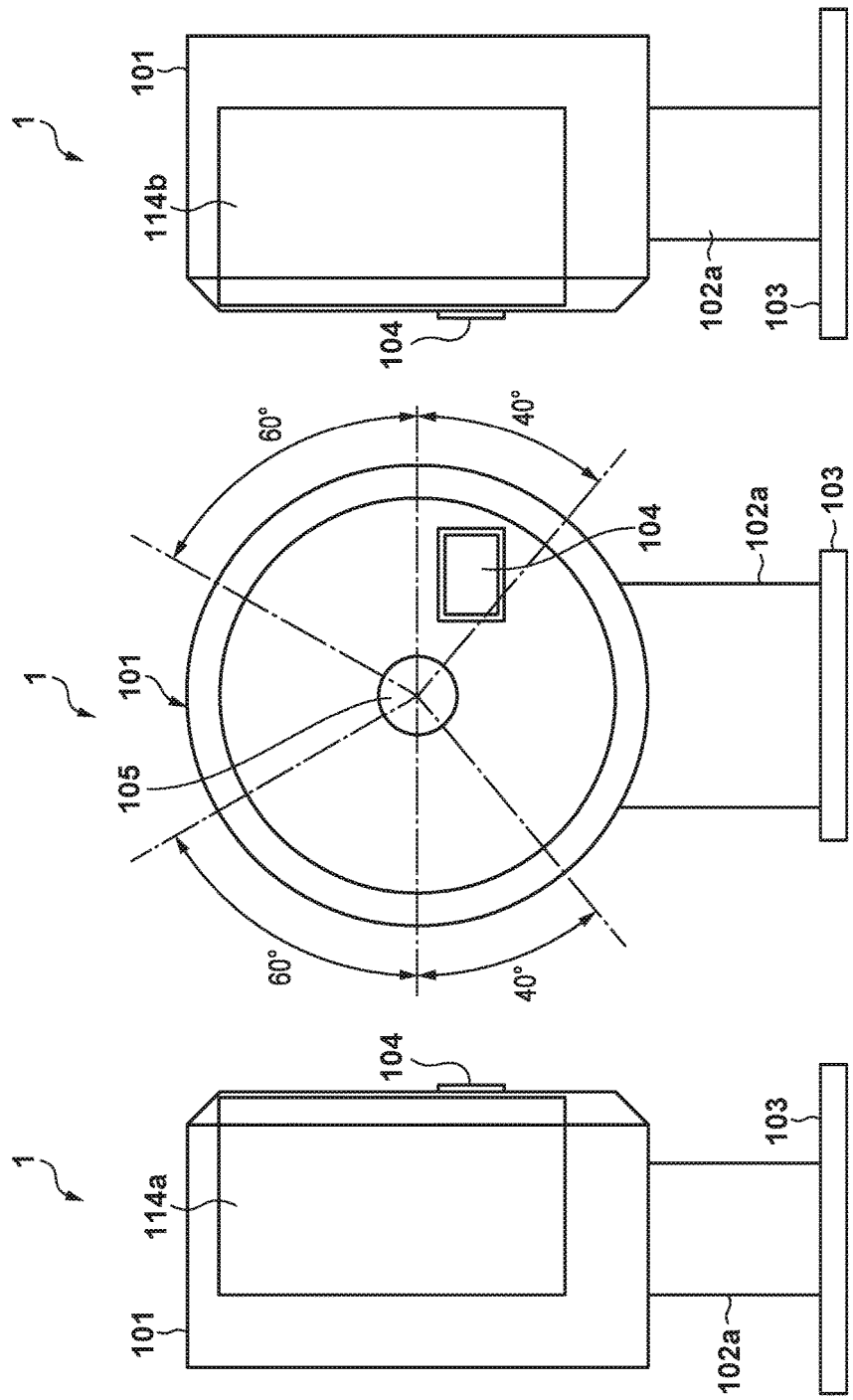

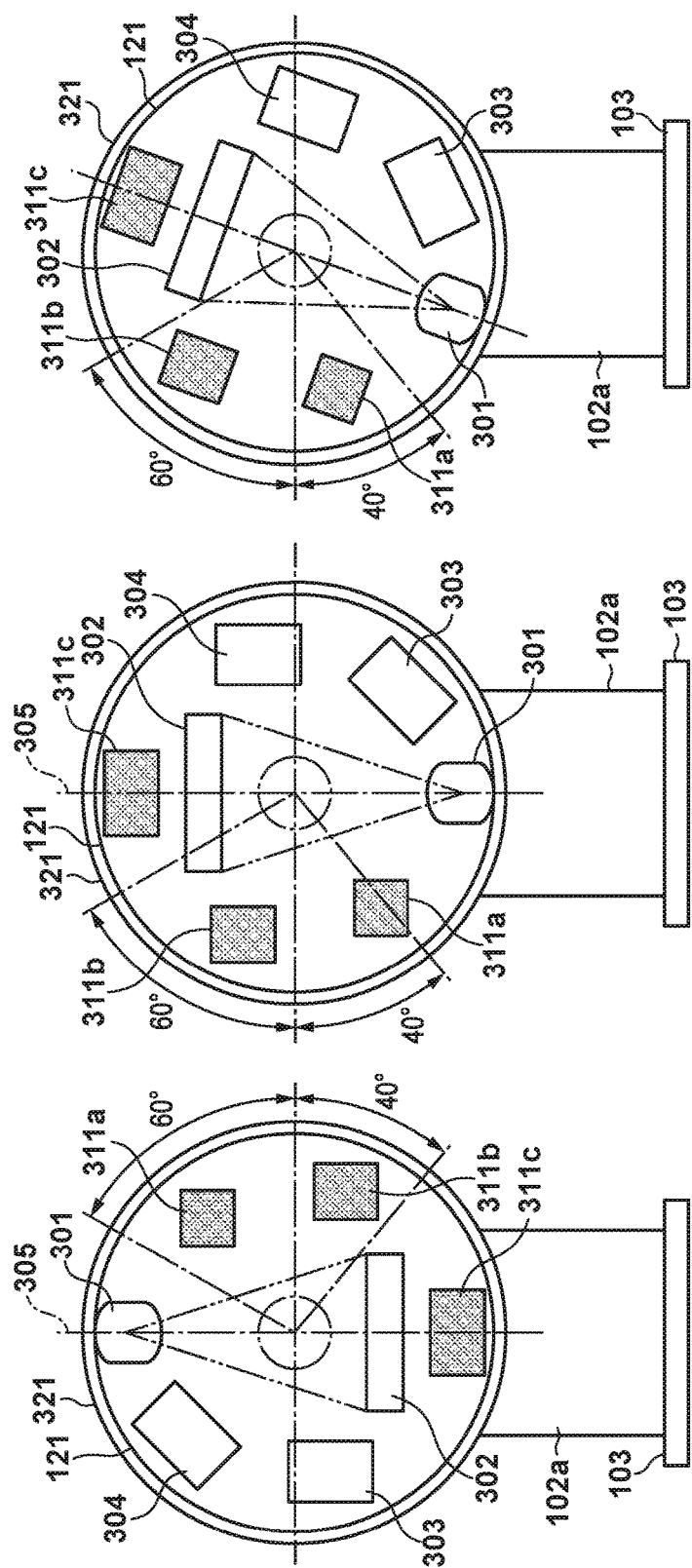

RADIATION CT APPARATUS AND METHOD OF CONTROLLING THE SAME

BACKGROUND OF THE INVENTION

Field of the Invention

The present invention relates to a radiation computed tomography apparatus (radiation CT apparatus) and a method of controlling the same.

Description of the Related Art

As an X-ray imaging apparatus for a breast cancer, a mammography apparatus is normally used. However, the sensitivity and specificity of a mammogram are known to be low for a dense breast (a breast with many mammary glands) because a morbid portion and a mammary structure overlap. As technologies for compensating for the disadvantage of the mammogram, tomosynthesis and a CBCT apparatus dedicated for breast have received attention.

Japanese Patent Laid-Open No. 2013-538668 (to be referred to as literature 1 hereinafter) discloses a multimode system that captures a breast of an object in one or more modes out of a CT mode, a narrow-angle tomosynthesis mode, a wide-angle tomosynthesis mode, and a mammography mode using a single apparatus.

Configuring a breast CBCT inspection in a standing position is advantageous from the viewpoint of a burden on an object or throughput, as disclosed in literature 1.

When performing CT imaging of a breast, the imaging technician needs to touch most of the breast to adjust the position of the breast. In literature 1, no consideration is given at all to the imaging technician's access to a breast inserted into a gantry (shield).

SUMMARY OF THE INVENTION

An embodiment of the present invention provides a radiation CT apparatus that allows an imaging technician to easily access, from a lateral direction of a gantry, a breast of an object inserted into the gantry.

According to one aspect of the present invention, there is provided a radiation CT apparatus comprising: a rotation unit configured to rotate about a rotation axis; a radiation generation unit and a radiation detector which are fixed on either side of the rotation axis in the rotation unit; and a gantry cover containing the radiation generation unit and the radiation detector and including a breast insert portion configured to insert a breast of an object, wherein an opening portion that can be opened and closed is placed on the gantry cover, and the rotation unit is stopped to form a space that allows a user to access the breast insert portion from the opening portion.

According to another aspect of the present invention, there is provided a radiation CT apparatus comprising: a rotation unit configured to rotate about a rotation axis; a radiation generation unit and a radiation detector which are fixed on either side of the rotation axis in the rotation unit; a gantry cover containing the radiation generation unit and the radiation detector and including a breast insert portion configured to insert a breast of an object; and a moving unit configured to move a counter weight arranged on the rotation unit.

According to one aspect of the present invention, there is provided a method of controlling a radiation CT apparatus including: a rotation unit configured to rotate about a rotation axis; a radiation generation unit and a radiation detector which are fixed on either side of the rotation axis in the rotation unit; and a gantry cover containing the radiation generation unit and the radiation detector, including a breast insert portion configured to insert a breast of an object, and including an opening portion that can be opened and closed, the method comprising: stopping the rotation unit, wherein when the rotation unit is stopped in the stopping, the radiation generation unit and the radiation detector are stopped to form a space that allows a user to access the breast insert portion from the opening portion.

Furthermore, according to another aspect of the present invention, there is provided a method of controlling a radiation CT apparatus including: a rotation unit configured to rotate about a rotation axis; a radiation generation unit and a radiation detector which are fixed on either side of the rotation axis in the rotation unit; and a gantry cover containing the radiation generation unit and the radiation detector, including a breast insert portion configured to insert a breast of an object, and including an opening portion that can be opened and closed, the method comprising: stopping the rotation unit at a specific rotation position; and moving a counter weight arranged on the rotation unit to form a space that allows a user to access the breast insert portion from the opening portion in a state in which the rotation unit is stopped at the specific rotation position.

Further features of the present invention will become apparent from the following description of exemplary embodiments (with reference to the attached drawings).

BRIEF DESCRIPTION OF THE DRAWINGS

FIGS. 1A to 1C are views showing the outer appearance of a breast CBCT apparatus according to the first embodiment;

FIGS. 3A and 3B are views showing the structure in the gantry of the breast CBCT apparatus according to the first embodiment;

FIGS. 5A to 5C are views showing the outer appearance of a breast CBCT apparatus according to the third embodiment;

FIGS. 6A to 6C are views showing the structure in the gantry of the breast CBCT apparatus according to the third embodiment;

DESCRIPTION OF THE EMBODIMENTS

Figure 2A:
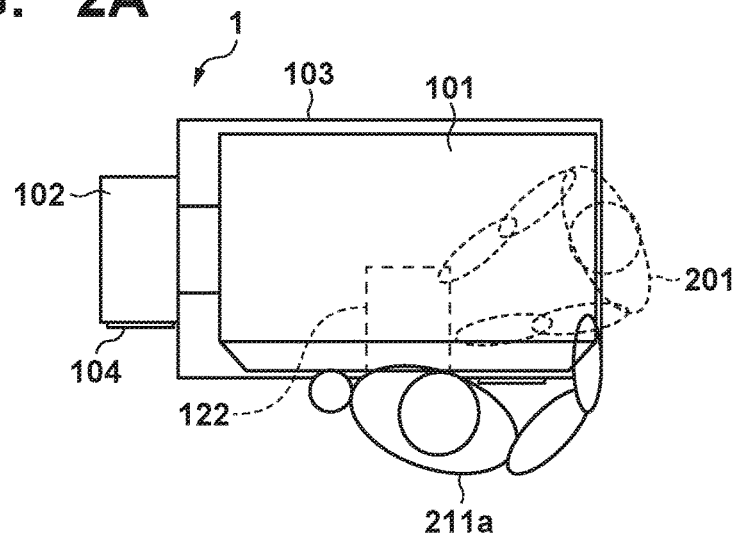
FIGS. 2A and 2B are views for explaining the operation of an imaging technician in the breast CBCT apparatus.

Preferred embodiments of the present invention will now be described with reference to the accompanying drawings. A cone beam CT apparatus (to be referred to as a breast CBCT apparatus hereinafter) will be exemplified below as a radiation CT apparatus. Note that as radiation, for example, X-rays are used.

<First Embodiment>

FIGS. 1A to 1C show the outer appearance of a breast CBCT apparatus 1 according to the first embodiment. FIG.

1A is a view of the breast CBCT apparatus viewed from the front side, FIG. 1B is a view of the breast CBCT apparatus viewed from the right side, and FIG. 1C is a view showing a state in which a door on the side surface of a gantry 101 is opened. In the breast CBCT apparatus 1, the gantry 101 is coupled with a gantry support unit 102 to be vertically movable and tiltable. The gantry support unit 102 is fixed to a base 103. Note that the base 103 may be provided with casters so as to be portable. An operation panel 104 is arranged on each of the gantry 101 and the gantry support unit 102. An imaging technician as a user can instruct to vertically move and tilt the gantry 101 or open and close a door 114 on the side surface of the gantry 101 by operating the operation panel 104.

The gantry 101 is covered by a gantry cover 113. A rotation unit 121 that rotates about a rotation axis 325 is attached inside the gantry cover 113. A radiation tube 301, a radiation detector 302, and the like are mounted on the board surface of the rotation unit 121. Out of the gantry cover 113, a portion that an object contacts when capturing a breast is called a front cover 111, and a portion that forms the side surface of the gantry 101 is called a side cover 112. A breast insert portion 105 is provided at the center of the front cover 111. A breast base 122 used to place the breast of the object is provided in the gantry 101 around the breast insert portion 105. A breast base cover (not shown) may be provided above the breast base 122. This is because at the time of CT imaging, the radiation detector 302 (FIGS. 3A and 3B) that passes above the breast of the object may contact the breast of the object. However, when the imaging technician accesses the breast of the object, the breast base cover needs to be removed. As described above, the gantry cover 113 includes the front cover 111 facing the board surface of the rotation unit 121, and forms the outside shape of the gantry 101 containing the radiation tube 301, the radiation detector 302, and counter weights 311a to 311c (FIGS. 3A and 3B).

The side surface (side cover 112) of the gantry cover 113 has an opening 120 configured to make the inside and outside of the gantry 101 communicate, and also includes the door 114 to open and close the opening 120. When the door 114 is opened, the opening 120 appears, as shown in FIG. 1C. As described above, the gantry cover 113 of the breast CBCT apparatus 1 according to this embodiment contains the radiation tube 301 serving as a radiation generation unit and the radiation detector 302. The gantry cover 113 also includes the breast insert portion 105 configured to insert the breast of the object. The opening 120 serving as an opening portion that can be opened and closed is placed on the periphery of the breast insert portion 105. In the breast CBCT apparatus 1 according to this embodiment, when the rotation unit 121 is stopped at an appropriate position, the radiation tube 301 serving as a radiation generation unit and the radiation detector 302 are stopped to form a space that allows the user to access the breast insert portion 105 from the opening 120 serving as an opening portion. Hence, in the stop state, the imaging technician can insert an arm into the gantry 101 from the opening 120 on the side surface of the gantry 101 and position the breast of the object in the imaging region. A door sensor 115 detects the open/closed state of the door 114. The structure with the opening 120 provided in the gantry cover 113 is different from that of conventional CT. This aims at allowing the imaging technician to access the breast of the object via the opening 120. However, when the breast base 122 that has an open top to enable access to the breast of the object is employed, the breast base cover (not shown) is needed from a safety requirement.

FIGS. 2A to 2D show examples of the positions of an object and an imaging technician when positioning an object breast in the imaging region. In this embodiment, the diameter of the gantry 101 is about 1.2 m. FIGS. 2A to 2D show examples in which an imaging technician 201 inserts both arms. However, the imaging technician 201 may insert one arm to exercise a technique. An object 211a or 211b inserts a breast into the breast insert portion 105 (FIGS. 1A to 1C) provided in the front cover 111 of the gantry 101. Before inserting the breast, the imaging technician 201 opens the door 114 of the opening 120 provided on the side surface of the gantry 101. The imaging technician 201 then inserts the arm from the opening 120 into the gantry 101 and positions the object breast on the breast base 122.

Figure 2B:
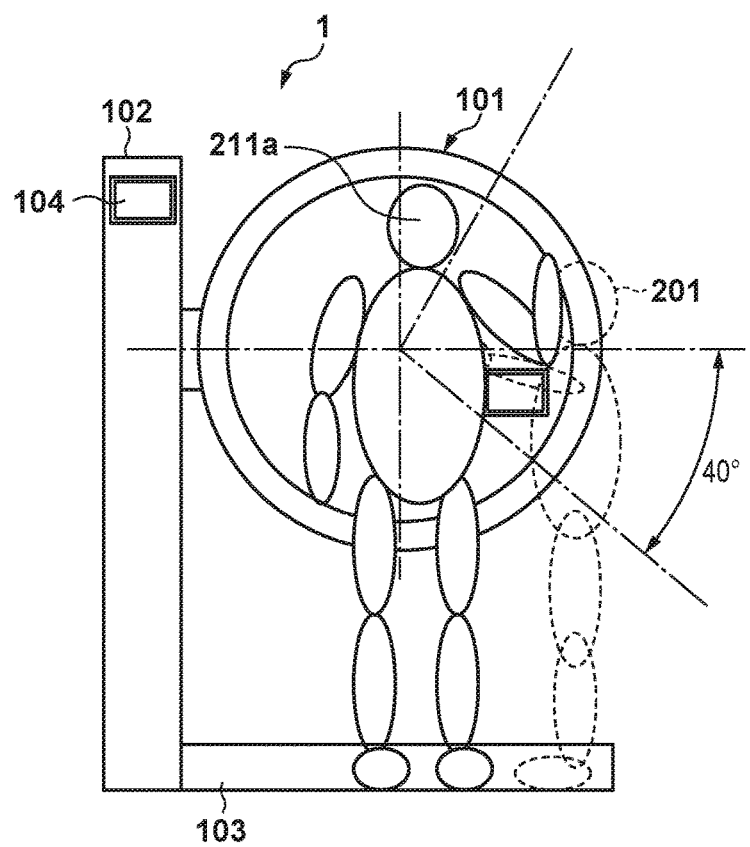

FIGS. 2A and 2B shows the technique of the imaging technician 201 who is shorter than the object 211a. FIG. 2A is a view of the technique viewed from above the breast CBCT apparatus 1, and FIG. 2B is a view of the technique viewed from the front of the breast CBCT apparatus 1. In the case of FIGS. 2A and 2B, the imaging technician 201 accesses the object breast located at a rather high position. In this case, to make the imaging technician 201 access the object breast without any problem, an opening of about 40° or more preferably exists on the lower side of a horizontal line.

Figure 2C:
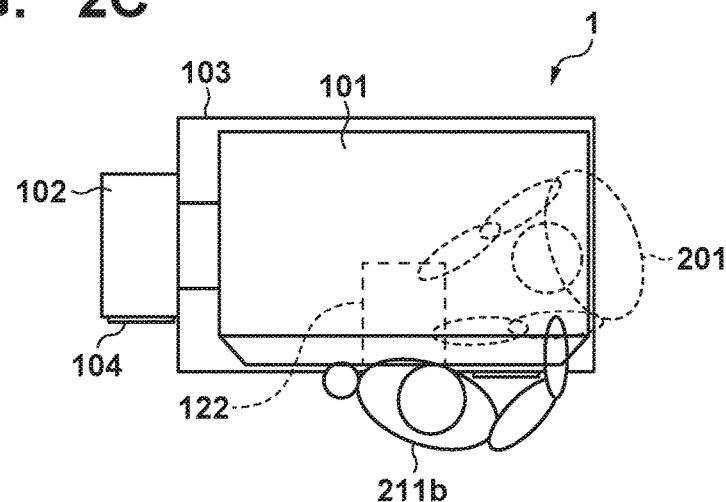
FIGS. 2C and 2D are views for explaining the operation of an imaging technician in the breast CBCT apparatus.
Figure 2D:
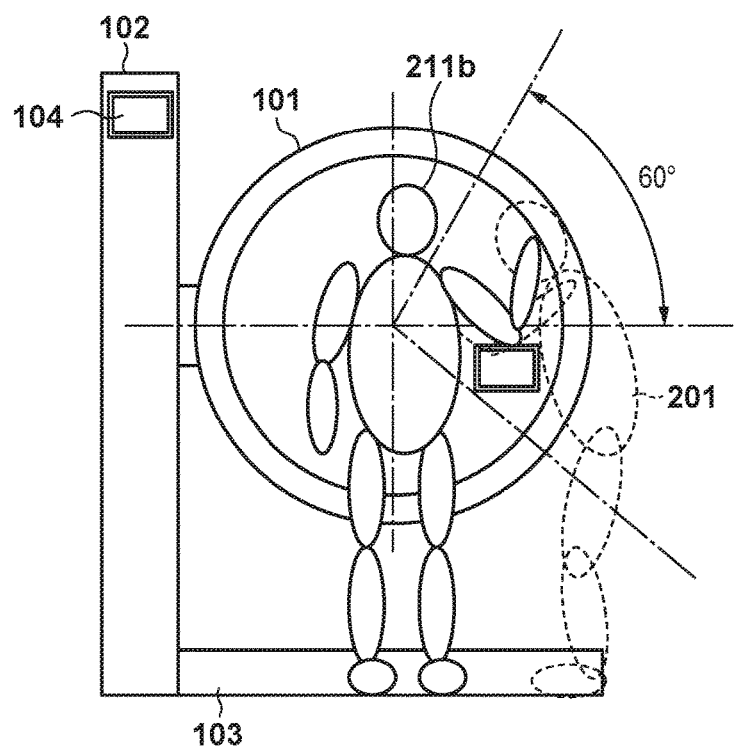

FIGS. 2C and 2D shows the technique of the imaging technician 201 who is taller than the object 211b. FIG. 2C is a view of the technique viewed from above the breast CBCT apparatus 1, and FIG. 2D is a view of the technique viewed from the front of the breast CBCT apparatus 1. In the case of FIGS. 2C and 2D, the imaging technician 201 accesses the object breast located at a rather low position. In this case, to make the imaging technician 201 access the object breast without any problem, an opening of about 60° or more preferably exists on the upper side of a horizontal line.

To cope with objects of various physical features, the opening angle of the opening 120 is preferably 100° (40° on the lower side+60° on the upper side) or more. When the imaging technician 201 inserts both arms into the gantry 101, the width of the opening 120 is preferably about 400 mm or more, as shown in FIG. 1C. When the imaging technician 201 accesses the object breast inserted into the gantry 101, the width of the space around the breast base 122 in the gantry 101 is preferably about 300 mm or more, as shown in FIG. 1C. However, the above-described sizes are merely examples, and the embodiment is not limited to these.

FIGS. 3A and 3B explain the internal structure of the gantry 101 according to the first embodiment. FIG. 3A shows a state in which the gantry cover 113 of the gantry 101 is removed, and the inside of the gantry 101 is viewed from the front. FIG. 3B shows the gantry 101 viewed from a side. In the gantry cover 113, the rotation unit 121 that rotates about the rotation axis 325 is arranged. The radiation tube 301 serving as a radiation generation unit and the radiation detector 302 are arranged and fixed on either side of the rotation axis 325 in the rotation unit 121 so as to face each other. The rotation unit 121 rotates to do radiation imaging of the inserted object breast from multiple directions. The rotation angle of the rotation unit 121 is 360° or more. In a half scan system, the rotation angle can be 180°+fan angle.

Electric units such as a radiation control unit 303 and a data collecting unit 304 are fixed on the board surface of the rotation unit 121. In addition, one or a plurality of counter weights (in this embodiment, the counter weights 311a to 311c) configured to adjust the rotation balance of the rotation unit 121 are fixed on the board surface of the rotation unit 121. Note that the radiation control unit 303 and the data collecting unit 304 may be integrated with the radiation tube 301 and the radiation detector 302, respectively. As described above, the radiation tube 301 and the radiation detector 302 are arranged on either side of the rotation center (rotation axis 325) of the rotation unit 121 while facing each other. A line that connects the radiation focus of the radiation tube 301 and the rotation center of the radiation detector 302 is called a center line 305.

Figure 8:
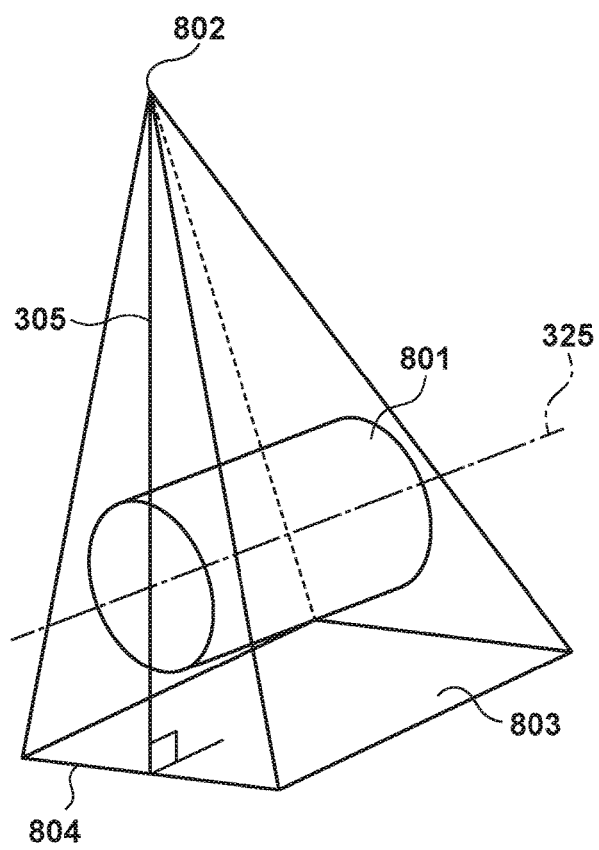
FIG. 8 is a view for explaining the imaging area of the breast CBCT apparatus.

FIG. 8 is a view for explaining an imaging region 801. The imaging region 801 is decided by a radiation focus 802 of the radiation tube 301, a light receiving area 803 of the radiation detector 302, and the rotation axis 325. Radiation emitted from the radiation focus 802 is shaped into a rectangle by a radiation aperture (not shown) and projected onto the radiation detector 302. The imaging region 801 is decided by the rotation axis 325 passing through the radiation having a quadrangular pyramid shape. Note that the positional relationship of the radiation tube 301 and the radiation detector 302 with respect to the rotation axis is set such that the center line 305 reaches almost the center of an edge 804 of the light receiving area 803 of the radiation detector 302 on the side of the front cover 111.

The breast base 122 is a table used to place the object breast inserted from the breast insert portion 105 into the gantry 101 during imaging, and is arranged in the imaging region. The breast base 122 is supported from a fixed unit 321 or the front cover 111 and fixed in the space even during the rotation of the rotation unit 121.

In this embodiment, a space that the user can access from the side surface of the gantry cover 113 to the imaging region 801 formed by the radiation tube 301 and the radiation detector 302 is formed between the front cover 111 and the board surface of the rotation unit 121. For this purpose, out of one or a plurality of counter weights, a counter weight arranged in the space has a limited height in the axial direction of the rotation axis 325. The counter weight arranged in the space is the counter weight arranged in a region of the board surface of the rotation unit 121 divided by two line segments 361 and 362 intersecting at an angle of 100° or more on the rotation axis 325 of the rotation unit 121. Note that the angle of 100° corresponds to the above-described opening 120 with an angle of 40° on the lower side of the horizontal line and 60° on the upper side.

In general, the radiation tube 301, the radiation detector 302, the radiation control unit 303, and the data collecting unit 304 are high in the rotation axis direction. This is because the area on the rotation unit 121 is limited. Hence, in this embodiment, electric units (for example, the radiation control unit 303 and the data collecting unit 304) for the radiation tube 301 and the radiation detector 302 are arranged outside the space. More specifically, in this embodiment, the space and the electric units are arranged on either side of the center line that connects the radiation focus of the radiation tube 301 and the rotation axis 325.

The heights of the radiation tube 301 and the radiation detector 302 in the rotation axis direction are about 300 mm, and the heights of the radiation control unit 303 and the data collecting unit 304 in the rotation axis direction are about 200 mm. As described with reference to FIGS. 1A to 1C and 2A to 2D, to make the imaging technician access the object breast inserted into the gantry 101, the width of the space around the breast base 122 is preferably about 300 mm or more. Assume that the interval from the front surface of the rotation unit 121 to the back surface of the front cover 111 is 350 mm. To make the imaging technician access the object breast, the radiation control unit 303 and the data collecting unit 304 need to be arranged on one side of the center line 305.

If heavy items (the radiation control unit 303 and the data collecting unit 304) are arranged on one side of the center line 305, the rotation balance is poor. To prevent this, the counter weights 311a and 311b are arranged on the opposite side of the radiation control unit 303 and the data collecting unit 304 with respect to the center line 305. Each of the low-profile counter weights 311a and 311b is made of a block of a metal with a high specific gravity, such as iron, lead, or tungsten. The weights and positions of the counter weights 311a to 311c may be decided by calculation from the viewpoint of design, or may be decided by actually rotating the rotation unit 121 such that the rotation speed of the rotation unit 121 or the current of a rotation motor 322 becomes constant.

As described above, in this embodiment, high-profile members such as the radiation control unit 303 and the data collecting unit 304 are arranged on one side divided by the center line 305, and the low-profile counter weights 311a and 311b are arranged on the other side. When the imaging technician accesses the imaging region 801 in the gantry 101, the rotation unit 121 needs to be at rest such that the low-profile counter weights 311a and 311b face the opening 120. Hence, a controller mounted on or connected to the breast CBCT apparatus 1 controls to stop the rotation unit 121 at a specific rotation position at which the above-described space for access and the outside of the gantry 101 communicate via the opening 120.

In the breast CBCT apparatus 1 according to this embodiment, since the gantry support unit 102 is located on the left side of the gantry 101, the opening 120 is provided on the right side of the gantry 101. The reset position of the rotation unit 121 may be the position shown in FIG. 3A. Alternatively, when an operation to open the door 114 of the opening 120 is performed on the operation panel 104, the rotation unit 121 may rotate up to the position shown in FIG. 3A before the door 114 opens.

Referring to FIG. 3B, the fixed unit 321 is connected to the gantry support unit 102 (FIGS. 1A to 1C) to be vertically movable and tiltable. A rotation shaft 324 is fixed to the fixed unit 321, and the rotation unit 121 is connected to the rotation shaft 324 via a bearing (not shown). The central axis of the rotation shaft 324 is the rotation axis 325. The rotation unit 121 is rotated by driving the rotation motor 322 fixed to the fixed unit 321. That is, when a gear 323a mounted on the drive shaft of the rotation motor 322 rotates, a ring-shaped gear 323b meshed with the gear 323a rotates. The ring-shaped gear 323b is fixed to the rotation unit 121. Hence, when the gear 323a rotates, the rotation unit 121 rotates about the rotation axis 325.

In the rotation unit 121, the radiation tube 301 and the radiation detector 302 are arranged on either side of the rotation center. The radiation control unit 303 and the data collecting unit 304 that are high-profile members are arranged on the far side of the center line 305 formed by the radiation tube 301 and the radiation detector 302. The low-profile counter weights 311a and 311b are arranged on the near side of the center line 305. In FIG. 3B, the near side corresponds to the position of the opening 120 of the gantry 101. In a state in which at least the opening 120 is open, the rotation unit 121 is at rest, as shown in FIGS. 3A and 3B. When the two conditions described above are met, the imaging technician can access, from the opening 120, the object breast inserted into the gantry 101.

Figure 9:
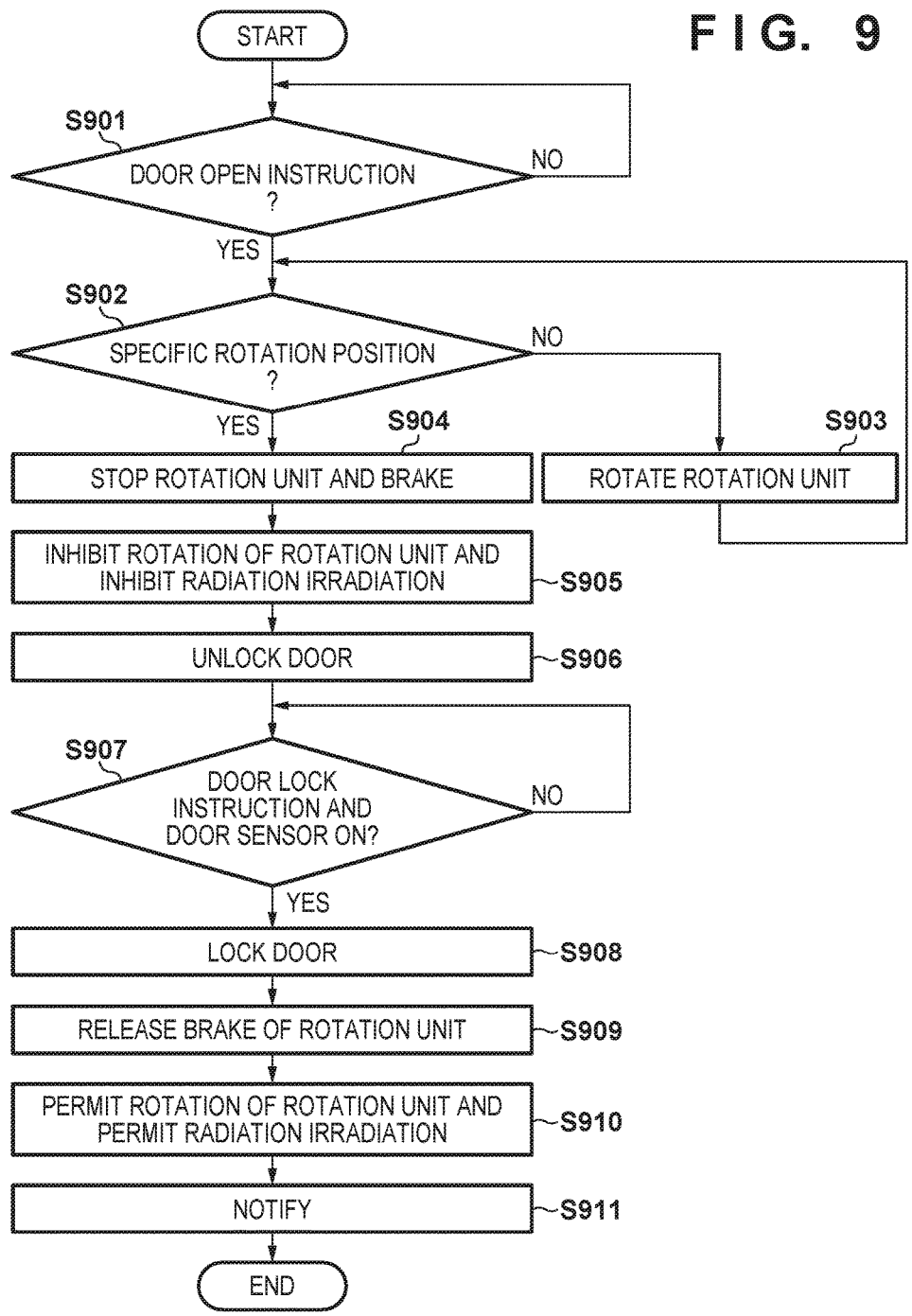
FIG. 9 is a flowchart for explaining processing of the breast CBCT apparatus at the time of opening and closing a door.

FIG. 9 is a flowchart for explaining processing at the time of opening and closing the door 114 according to the first embodiment. Note that the processing shown in FIG. 9 is implemented when, for example, the CPU (not shown) of the controller mounted on or connected to the breast CBCT apparatus 1 executes a program stored in a ROM (not shown). According to a user instruction to open the door 114 which is input by the imaging technician by operating the operation panel 104, the controller stops the rotation unit 121 at a specific rotation position and then sets the door 114 in an unlocked state (steps S901 to S906). The specific rotation position is the rotation position at which the space for access and the outside of the gantry 101 communicate via the opening 120, as described above. In addition, according to a user instruction to lock the door 114, the controller confirms the closed state of the door 114 and sets the door 114 in a locked state, and then, permits the rotation unit 121 to rotate (steps S907 to S910). Each step will be described in detail.

Upon receiving a user instruction to open the door, the process advances from step S901 to step S902. In step S902, the controller determines whether the rotation unit 121 is located at the specific rotation position. The specific rotation position of the rotation unit 121 is, for example, the rotation position as shown in FIG. 3A. Detection of the specific rotation position is implemented by a method of detecting it using a photointerrupter or a method of specifying the rotation position from a signal of a rotary encoder connected to the rotation motor 322. Upon determining that the rotation unit 121 is not located at the specific rotation position, the process advances to step S903, and the controller drives the rotation motor 322 to rotate the rotation unit 121 up to the specific rotation position. Upon determining in step S902 that the rotation unit 121 is located at the specific rotation position, the process advances to step S904.

In step S904, the controller stops the rotation motor 322 and operates a brake (not shown) to maintain the resting state of the rotation unit 121. In step S905, the controller inhibits the rotation operation of the rotation unit 121. Accordingly, any instruction to do the rotation operation of the rotation unit 121 is refused. That is, the controller inhibits the rotation of the rotation unit 121 during the unlocked state of the door 114. The controller also inhibits radiation irradiation from the radiation tube 301 during the unlocked state of the door 114. In step S906, the controller unlocks the door 114. In this state, the user can open the door 114 and access the inside of the gantry 101 from the opening 120.

After that, when an instruction to lock the door 114 is input from the operation panel 104, and the door sensor 115 detects that the door 114 is closed, the process advances from step S907 to step S908. The controller sets the door 114 in a locked state in step S908, and releases the brake of the rotation unit 121 in step S909. The controller then notifies the user via the operation panel 104 that the rotation is permitted.

As described above, according to the breast CBCT apparatus 1 of the first embodiment, the rotation unit 121 is stopped not to arrange the radiation generation unit and the radiation detector between the opening 120 and the breast insert portion 105. In addition, the arrangement of the electric units and the heights of the counter weights are defined, thereby forming the space to access the imaging region between the front cover 111 and the board surface of the rotation unit 121. Control is performed to stop the rotation unit 121 at the position at which the space communicates with the outside of the gantry 101 via the opening 120 on the side surface of the gantry 101. Hence, the imaging technician who is the user can access the imaging region in the gantry 101 from the side surface of the gantry 101, and the operability in the technique of breast CBCT imaging improves. Note that in the above embodiment, the low-profile counter weights are arranged in the space. However, the components fixed to the rotation unit 121 may be inhibited from being arranged between the opening 120 and the breast insert portion 105.

<Second Embodiment>

In the first embodiment, a case has been described in which the gantry support unit 102 is provided on the left side when viewed from the front of the breast CBCT apparatus 1, the left side of the gantry 101 is fixed to the gantry support unit 102, and the opening 120 is provided on the right side surface of the gantry 101. However, the present invention is not limited to this. For example, the right side of the gantry 101 may be connected to the gantry support unit 102, and the opening 120 may be provided on the left side of the gantry 101. In the second embodiment, a breast CBCT apparatus having such an arrangement will be described.

Figure 4A:
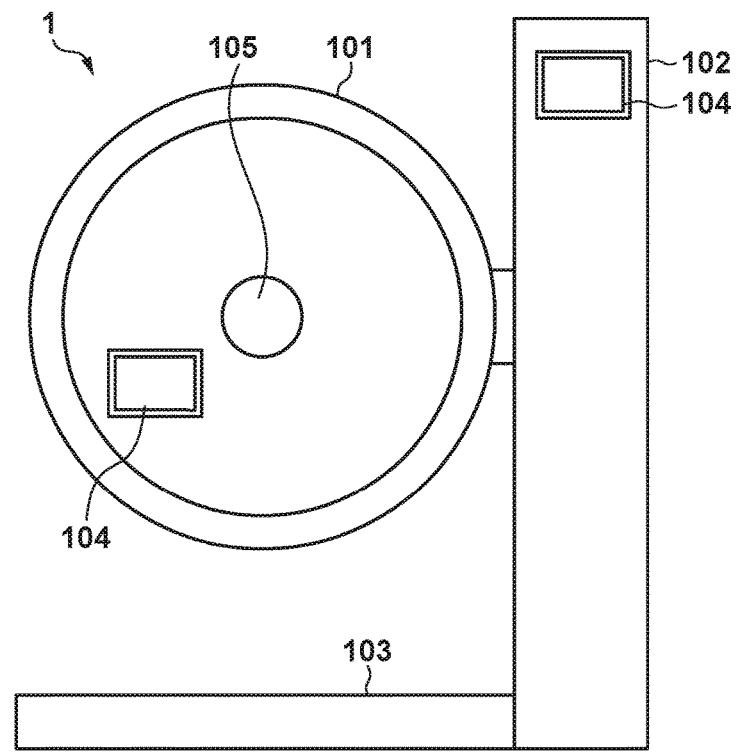
FIGS. 4A and 4B are views for explaining a breast CBCT apparatus according to the second embodiment.
Figure 4B:
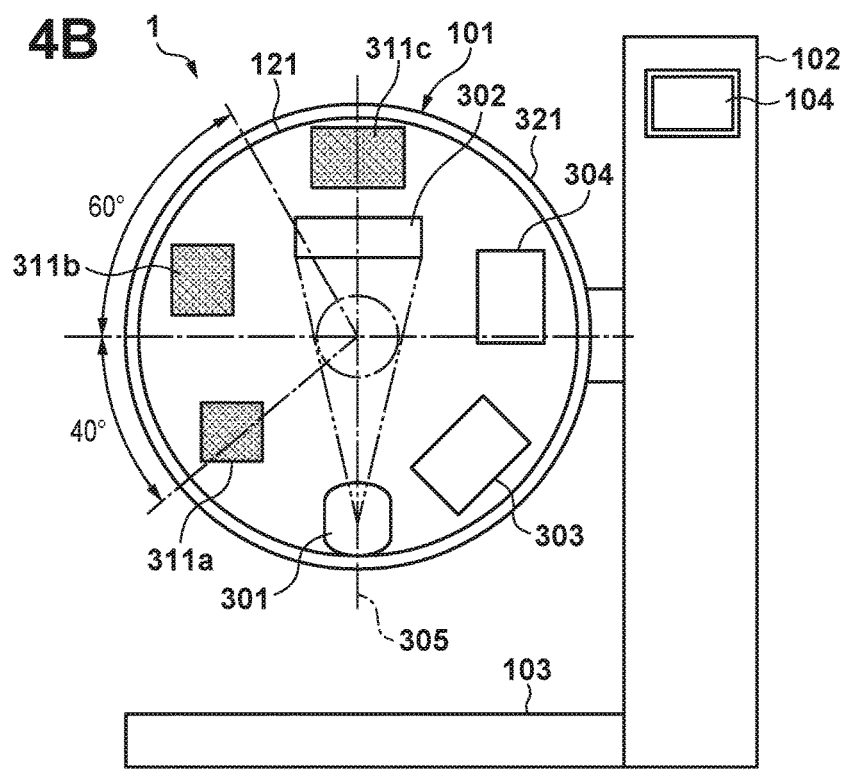

FIGS. 4A and 4B explain a breast CBCT apparatus according to the second embodiment. FIG. 4A is a front view showing the outer appearance of a breast CBCT apparatus 1. FIG. 4B is a front view showing a state in which a gantry cover 113 is removed from a gantry 101. As in the first embodiment, a rotation unit 121 is rotatably arranged in the gantry cover 113. A radiation tube 301, a radiation detector 302, a radiation control unit 303, a data collecting unit 304, and counter weights 311a and 311b are fixed to the rotation unit 121.

In the example of FIGS. 4A and 4B, since a gantry support unit 102 is located on the right side of the gantry 101, an opening 120 is provided on the left side of the gantry 101. For this reason, unlike the first embodiment, when an imaging technician opens the opening 120 of the gantry 101 and accesses an object breast, the rotation unit 121 is stopped in a state in which the radiation detector 302 is located on the upper side of the rotation unit 121, and the radiation tube 301 is located on the lower side. In this state, the radiation control unit 303 and the data collecting unit 304 that are high-profile members are arranged on the right side of a center line 305. In addition, the low-profile counter weights 311a and 311b are arranged on the left side of the center line 305. When the imaging technician accesses, the rotation unit 121 needs to be at rest such that the low-profile counter weights 311a and 311b face the opening 120, as shown in FIG. 4B.

Note that processing by a controller according to the second embodiment is the same as in the first embodiment (FIG. 9). However, the specific position of the rotation unit 121 determined in step S902 changes by 180° from that in the first embodiment.

The first and second embodiments are different in the relationship between the opening angle of the opening 120 and the radiation tube 301 and the radiation detector 302. As conceptually illustrated in FIGS. 3A and 3B and FIGS. 4A and 4B, the width of the radiation detector 302 is generally larger than the width of the radiation tube 301. As described with reference to FIGS. 2A to 2D, the opening angle is preferably 60° or more on the upper side and 40° or more on the lower side of a horizontal axis. Since the angle necessary on the lower side of the horizontal axis is smaller, the design can be made easy by locating the radiation detector 302 on the lower side when the imaging technician accesses. However, if the width of the radiation detector 302 is smaller than the width of the radiation tube 301, the second embodiment is preferable.

<Third Embodiment>

In the first and second embodiments, a case in which one opening 120 is provided on the side surface of the gantry 101 has been described. However, the present invention is not limited to this. In the third embodiment, a breast CBCT apparatus having a plurality of openings 120 on the side surface of a gantry 101 will be described. FIGS. 5A to 5C show the outer appearance of a breast CBCT apparatus 1 according to the third embodiment. FIG. 5A is a left side view of the breast CBCT apparatus 1 according to the third embodiment. FIG. 5B is a front view of the breast CBCT apparatus 1 according to the third embodiment. FIG. 5C is a right side view of the breast CBCT apparatus 1 according to the third embodiment. In the first or second embodiment, a gantry support unit 102 is located on a side of the gantry 101. In the third embodiment, the gantry support unit 102 is located under the gantry 101. As the advantage in this case, the opening 120 to access an object breast can be provided on either side. Hence, the breast CBCT apparatus 1 according to the third embodiment has the openings 120 on the left and right sides of the gantry 101. A door 114a is provided on the opening 120 on the left side of the gantry 101, and a door 114b is provided on the opening 120 on the right side.

FIG. 6A is a view for explaining the stop state of a rotation unit 121. When opening the door 114b on the right side surface of the gantry 101 and accessing the object breast, the rotation unit 121 is stopped such that low-profile counter weights 311a and 311b are located on the right side, as in the first embodiment (see FIG. 6A). On the other hand, when opening the door 114a on the left side surface of the gantry 101 and accessing the object breast, the rotation unit 121 is stopped such that the low-profile counter weights 311a and 311b are located on the left side (see FIG. 6B). However, if the width of a radiation detector 302 is larger than the width of a radiation tube 301, as discussed in the second embodiment, the rotation unit 121 is preferably rotated clockwise slightly from the state in FIG. 6B, as shown in FIG. 6C. This is because the opening angle is preferably 60° or more on the upper side and 40° or more on the lower side of a horizontal axis.

Processing at the time of opening and closing a door according to the third embodiment as described above will be explained using the flowchart of FIG. 9. A controller according to the third embodiment receives a user instruction to designate one of the plurality of openings 120 (in the embodiment, designate a door). The controller then controls to stop the rotation unit 121 at a specific rotation position at which the space to access the imaging region and the outside of the gantry 101 communicate via the designated opening 120.

That is, in the third embodiment, the imaging technician can designate, from an operation panel 104, which one of the doors 114a and 114b should be opened. Hence, the door open instruction includes information for designating the left door 114a or the right door 114b. The specific rotation position of the rotation unit 121 determined in step S902 changes depending on which one of the doors 114a and 114b is designated, as described with reference to FIGS. 6A to 6C. In the process of controlling the lock state of the door in steps S906 to S908, out of the doors 114a and 114b, the door designated from the operation panel 104 is controlled. The rest of the processing is the same as in the first embodiment.

<Fourth Embodiment>

In the first to third embodiments, the heights of the counter weights arranged in the space to access the imaging region are limited, and the counter weights are immovably arranged. In the fourth embodiment, the heights of the counter weights arranged in the space to access the imaging region are not limited, and the space is ensured by moving the counter weights. To do this, a breast CBCT apparatus 1 according to the fourth embodiment includes a moving mechanism configured to move a counter weight arranged on a rotation unit 121. For example, in the fourth embodiment, some or all of counter weights are moved out of a space to form, between a front cover 111 and the board surface of the rotation unit 121, a space that allows a user to access an imaging region from the side surface of a gantry 101. The breast CBCT apparatus 1 according to the fourth embodiment includes a moving mechanism configured to move a counter weight arranged on the rotation unit.

Figure 7A:
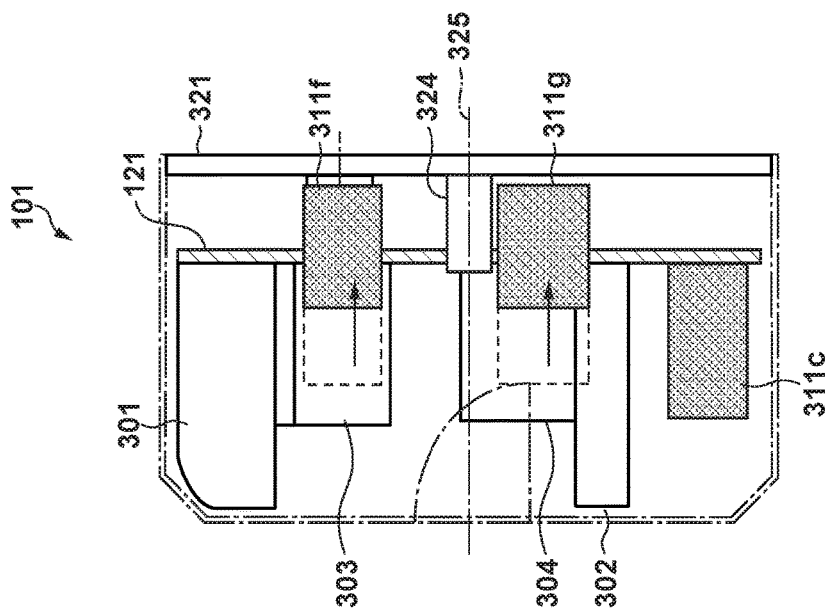
FIGS. 7A and 7B are views showing the structure in the gantry of a breast CBCT apparatus according to the fourth embodiment.

An arrangement for moving a counter weight arranged in the space to access the imaging region along the board surface of the rotation unit 121 will be described. FIG. 7A shows the member arrangement on the rotation unit 121 according to the fourth embodiment. In the fourth embodiment, counter weights 311d and 311e that have a relatively high-profile are used, unlike the first to third embodiments. As the advantage of using the counter weights 311d and 311e that have a relatively high-profile, it is easy to hold the rotation balance with respect to a radiation control unit 303 and a data collecting unit 304 that have a high-profile in the rotation axis direction. However, when the counter weights 311d and 311e that have a relatively high-profile are used, the accessibility to the object breast in the gantry 101 lowers. To prevent this, in the fourth embodiment, moving mechanisms 701a and 701b configured to retract the counter weights 311d and 311e to the periphery when opening a door 114 and accessing the object breast from the opening 120 are provided. That is, in the fourth embodiment, although it is easy to adjust the rotation balance using the counter weights 311d and 311e, the apparatus arrangement becomes complex because the moving mechanisms 701a and 701b are needed. Note that the counter weights 311d and 311e can be moved linearly or curvilinearly. The counter weights may be moved while being rotated, like the movement of the counter weight 311e.

Figure 7B:
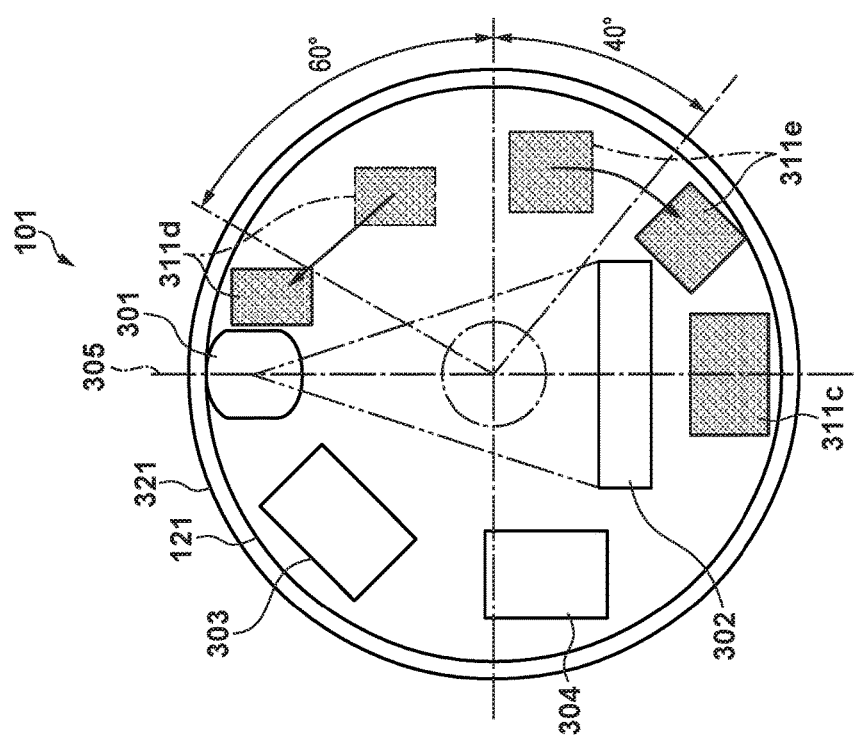

In the above embodiment, the counter weights are moved in the direction along the surface of the rotation unit 121. However, the present invention is not limited to this. For example, in FIG. 7B, the counter weights 311d and 311e are rotated in the rotation axis direction to improve the accessibility to the object breast, which lowers due to the use of the high-profile counter weights 311d and 311e. The board surface of the rotation unit 121 is provided with openings configured to pass counter weights 311f and 311g and a mechanism configured to move the counter weights in the axial direction of a rotation axis 325 through the openings provided in the board surface. In this case, it is only necessary to ensure a space to access the imaging region by the movement of the counter weights 311f and 311g. Hence, the counter weights need not wholly move to the outside of the space (the opposite side of the rotation unit 121). Note that the rotation unit 121 may become unrotatable when the counter weights 311f and 311g are moved. This is because when the door 114 of the opening 120 is open, rotating the rotation unit 121 in the exposed state of the opening 120 poses a safety problem, and therefore, the rotation of the rotation unit 121 is inhibited.

Note that as a modification, the counter weights 311f and 311g (to be referred to as counter weights 311 hereinafter)

themselves may deform in the rotation axis direction to move the center of gravity. For example, the counter weights 311 having a quadrangular prism shape may bend at an intermediate position in the height direction. Alternatively, the counter weights 311 may be formed like a pantograph to change the height in the rotation axis direction. At any rate, when opening the door 114, the counter weights 311 are deformed so as to be shortened in the rotation axis direction.

The opening/closing processing of the door 114 according to the fourth embodiment as described above is almost the same as in the first embodiment (FIG. 9). However, in step S904 or S905 before the door 114 is unlocked, the controller moves the counter weights as described with reference to FIG. 7A or 7B. In addition, in step S909 before the door 114 is locked again, the controller returns the counter weights to the initial state.

As described above, according to the fourth embodiment, even if the counter weights 311d to 311g that have a relatively high-profile are arranged on the side of the opening 120 when the rotation unit 121 stops, the accessibility to the object breast can be improved.

<Fifth Embodiment>

In the fourth embodiment, as a method of moving the counter weights, an arrangement for moving the counter weights while maintaining a state in which they are mounted on the rotation unit 121 has been described. However, the present invention is not limited to this. For example, a counter weight 311 may move from a rotation unit 121 to a door 114 that opens and closes an opening 120. In a state in which the opening 120 is closed by the door 114, a state as shown in FIG. 3A is obtained. When an instruction to open the opening 120 (door 114) is input from an operation panel 104, the counter weight 311 moves from the rotation unit 121 to the door 114 of the opening 120. The counter weight can be attached/detached to/from the rotation unit 121 or the door 114 using an electromagnet or the like. Note that the moving destination of the counter weight 311 is not limited to the door 114 and may be the inner wall of a gantry cover 113. In this case, for example, counter weights 311d and 311e are moved, as shown in FIG. 7A, and then moved to the inner wall of a side cover 112. Note that the rotation unit 121 may become unrotatable when the counter weights 311 are moved. This is because when the opening 120 is open, the rotation of the rotation unit 121 is inhibited.

According to the present invention, in a radiation CT apparatus, it is possible to access a breast as an object from a side surface of the gantry.

As described above, according to the embodiments, in the breast CBCT apparatus 1, the members on the rotation unit 121 are intentionally made to have height differences to enable access to the breast inserted into the gantry. That is, it is possible to obtain the effect of allowing the imaging technician to easily access to the breast from a side of the gantry 101 while holding the weight balance (rotation balance) of the entire rotation unit 121.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-131837, filed Jun. 30, 2015 which is hereby incorporated by reference herein in its entirety.

What is claimed is:

1. A radiation CT apparatus, comprising:
a rotation unit configured to rotate a radiation generation unit and a radiation detector about a rotation axis;
a gantry cover containing the radiation generation unit and the radiation detector:
a door configured to open and close an opening portion that is placed on the gantry cover; and
a control unit configured to control such that, when the door is opened, the rotation unit is stopped at a specific rotation position where a space that allows a user to access from the opening portion is formed, wherein
the rotation unit is stopped not to arrange the radiation generation unit and the radiation detector between the opening portion and a breast insert portion which the gantry cover includes.

2. The apparatus according to claim 1, wherein one or a plurality of counter weights configured to adjust a rotation balance of the rotation unit are fixed to the rotation unit, and
out of the one or the plurality of counter weights, a counter weight arranged in the space has a limited height in an axial direction of the rotation axis.

3. The apparatus according to claim 1, wherein the control unit stops the rotation unit at the specific rotation position and sets the door in an unlocked state in accordance with a user instruction to open the door.

4. The apparatus according to claim 3, wherein the control unit inhibits a rotation of the rotation unit during the unlocked state of the door.

5. The apparatus according to claim 3, wherein the control unit confirms a closed state of the door, sets door in a locked state, and permits the rotation of the rotation unit.

6. The apparatus according to claim 1, wherein the opening portion comprises a plurality of opening portions provided at a plurality of portions of a side surface of the gantry cover, and
the control unit receives a user instruction to designate one of the plurality of opening portions and controls to stop the rotation unit at the specific rotation position where the space is formed.

7. A radiation CT apparatus, comprising:
a rotation unit configured to rotate a radiation generation unit and a radiation detector about a rotation axis;
a gantry cover containing the radiation generation unit and the radiation detector:
a door configured to open and close an opening portion that is placed on the gantry cover; and
a control unit configured to control such that, when the door is opened, the rotation unit is stopped at a specific rotation position where a space that allows a user to access from the opening portion is formed, wherein
the rotation unit is stopped not to arrange a component fixed to the rotation unit between the opening portion and a breast insert portion which the gantry cover includes.

8. The apparatus according to claim 7, wherein the component comprises electric units for the radiation generation unit and the radiation detector.

9. The apparatus according to claim 8, wherein the electric units are arranged to sandwich, with the space, a center line that connects a radiation focus of the radiation generation unit and the rotation axis.

10. The apparatus according to claim 7, wherein one or a plurality of counter weights configured to adjust a rotation balance of the rotation unit are fixed to the rotation unit, and
out of the one or the plurality of counter weights, a counter weight arranged in the space has a limited height in an axial direction of the rotation axis.

11. The apparatus according to claim 7, wherein the control unit stops the rotation unit at the specific rotation position and sets the door in an unlocked state in accordance with a user instruction to open the door.

12. The apparatus according to claim 11, wherein the control unit inhibits a rotation of the rotation unit during the unlocked state of the door.

13. The apparatus according to claim 11, wherein the control unit confirms a closed state of the door, sets door in a locked state, and permits the rotation of the rotation unit.

14. The apparatus according to claim 7, wherein the opening portion comprises a plurality of opening portions provided at a plurality of portions of a side surface of the gantry cover, and
the control unit receives a user instruction to designate one of the plurality of opening portions and controls to stop the rotation unit at the specific rotation position where the space is formed.

15. A radiation CT apparatus, comprising:
a rotation unit configured to rotate a radiation generation unit and a radiation detector about a rotation axis;
a gantry cover containing the radiation generation unit and the radiation detector; and
a moving unit configured to move a counter weight arranged on the rotation unit, wherein
the moving unit moves the counter weight to form a space that allows a user to access from an opening portion provided on a side surface of the gantry cover, and
the rotation unit is stopped not to arrange the radiation generation unit and the radiation detector between the opening portion and a breast insert portion which the gantry cover includes.

16. The apparatus according to claim 15, wherein the moving unit moves the counter weight arranged in the space along a board surface of the rotation unit.

17. The apparatus according to claim 15, wherein a board surface of the rotation unit includes an opening portion configured to pass the counter weight arranged in the space, and
the moving unit moves the counter weight arranged in the space in an axial direction of the rotation axis through the opening portion provided in the board surface.

18. The apparatus according to claim 15, wherein the moving unit moves the counter weight arranged in the space to an inner wall of the gantry cover.

19. The apparatus according to claim 15, wherein the counter weight arranged in the space comprises a counter weight arranged in a region of a board surface of the rotation unit divided by two line segments intersecting at an angle of not less than 100 degrees on the rotation axis of the rotation unit.

20. A method of controlling a radiation CT apparatus including:
a rotation unit configured to rotate a radiation generation unit and a radiation detector about a rotation axis;
a gantry cover containing the radiation generation unit and the radiation detector; and
a door configured to open and close an opening portion that is placed on the gantry cover, the method comprising:
controlling such that, when the door is open, the rotation unit is stopped at a specific rotation position where a space that allows a user to access from the opening portion is formed, and
the rotation unit is stopped not to arrange the radiation generation unit and the radiation detector between the opening portion and a breast insert portion which the gantry cover includes.

21. A method of controlling a radiation CT apparatus including:
a rotation unit configured to rotate a radiation generation unit and a radiation detector about a rotation axis;
a gantry cover containing the radiation generation unit and the radiation detector, the method comprising:
stopping the rotation unit at a specific rotation position; and
moving a counter weight arranged on the rotation unit to form a space that allows a user to access the breast insert portion from the opening portion in a state in which the rotation unit is stopped at the specific rotation position, wherein
the rotation unit is stopped not to arrange the radiation generation unit and the radiation detector between the opening portion and a breast insert portion which the gantry cover includes.

22. A radiation CT apparatus, comprising:
a rotation unit configured to rotate a radiation generation unit and a radiation detector about a rotation axis;
a gantry cover containing the radiation generation unit and the radiation detector;
a door configured to open and close an opening portion that is placed on the gantry cover; and
a control unit configured to control such that the rotation unit is stopped at a specific rotation position where a space that allows a user to access from the opening portion is formed, wherein
the rotation unit is stopped not to arrange the radiation generation unit and the radiation detector between the opening portion and a breast insert portion which the gantry cover includes.

23. The apparatus according to claim 22, wherein the rotation unit is stopped not to arrange a component fixed to the rotation unit between the opening portion and a breast insert portion which the gantry cover includes.

24. The apparatus according to claim 22, wherein the control unit sets the door in an unlocked state.

25. The apparatus according to claim 24, wherein the control unit stops the rotation unit at the specific rotation position and sets the door in an unlocked state in accordance with a user instruction to open the door.

26. The apparatus according to claim 24, wherein the control unit inhibits a rotation of the rotation unit during the unlocked state of the door.

27. The apparatus according to claim 22, wherein the control unit confirms a closed state of the door, sets the door in a locked state, and permits the rotation of the rotation unit.

28. The apparatus according to claim 22, wherein the gantry cover comprises a front cover perpendicular to the rotation axis and a side cover connected to the front cover connected to the periphery of the front cover and parallel to the rotation axis, and the opening portion is placed on the side cover of the gantry cover.

29. A method of controlling a radiation CT apparatus, comprising:
   a rotation unit configured to rotate a radiation generation unit and a radiation detector about a rotation axis;
   a gantry cover containing the radiation generation unit and the radiation detector; and
   a door configured to open and close an opening portion that is placed on the gantry cover,
the method comprising:
   controlling such that the rotation unit is stopped at a specific rotation position where a space that allows a user to access from the opening portion is formed, wherein
   the rotation unit is stopped not to arrange the radiation generation unit and the radiation detector between the opening portion and a breast insert portion which the gantry cover includes.

* * * * *